(12) United States Patent
Castelltort et al.

(10) Patent No.: US 8,901,080 B2
(45) Date of Patent: Dec. 2, 2014

(54) CONJUGATE OF HYALURONIC ACID FOR COSMETIC TREATMENT AND PREPARATION METHOD

(75) Inventors: Marc Ramis Castelltort, Barcelona (ES); Isaac Ojea Jimenez, Barcelona (ES); Joaquin Querol Sastre, Barcelona (ES)

(73) Assignee: Endor Nanotechnologies, S.L., Barcelona (ES)

( * ) Notice: Subject to any disclaimer, the term of this patent is extended or adjusted under 35 U.S.C. 154(b) by 761 days.

(21) Appl. No.: 12/811,274

(22) PCT Filed: Jan. 5, 2009

(86) PCT No.: PCT/ES2009/000001
§ 371 (c)(1),
(2), (4) Date: Feb. 18, 2011

(87) PCT Pub. No.: WO2009/087254
PCT Pub. Date: Jul. 16, 2009

(65) Prior Publication Data
US 2011/0144030 A1    Jun. 16, 2011

(30) Foreign Application Priority Data
Jan. 4, 2008   (ES) .................................. 200800011

(51) Int. Cl.
| A61K 38/02 | (2006.01) |
| C08B 37/08 | (2006.01) |
| A61K 8/73 | (2006.01) |
| A61Q 19/00 | (2006.01) |
| C12P 19/28 | (2006.01) |
| A61K 8/02 | (2006.01) |
| A61K 8/11 | (2006.01) |
| A61K 8/19 | (2006.01) |
| A61K 8/29 | (2006.01) |
| B82Y 5/00 | (2011.01) |

(52) U.S. Cl.
CPC ............... *C08B 37/0072* (2013.01); *A61K 8/02* (2013.01); *A61K 8/11* (2013.01); *A61K 8/19* (2013.01); *A61K 8/29* (2013.01); *A61K 8/735* (2013.01); *A61Q 19/00* (2013.01); *B82Y 5/00* (2013.01); *A61K 2800/413* (2013.01); *A61K 2800/57* (2013.01); *A61K 2800/91* (2013.01); *Y10S 977/773* (2013.01); *Y10S 977/81* (2013.01); *Y10S 977/811* (2013.01); *Y10S 977/896* (2013.01); *Y10S 977/904* (2013.01)
USPC .......... 514/18.8; 514/42; 536/29.13; 435/85; 977/773; 977/810; 977/811; 977/896; 977/904

(58) Field of Classification Search
CPC ............. A61K 8/02; A61K 8/11; A61K 8/19; A61K 8/29; A61K 2800/57; A61K 2800/413; C08B 37/0072

USPC .......... 514/54; 536/29.13; 977/773, 810, 811, 977/896
See application file for complete search history.

(56) References Cited

U.S. PATENT DOCUMENTS

| 5,824,658 | A | * | 10/1998 | Falk et al. ........................ 514/54 |
| 6,989,157 | B2 | * | 1/2006 | Gillis et al. .................... 424/618 |
| 2002/0128512 | A1 | | 9/2002 | Bulpitt et al. |
| 2003/0064086 | A1 | * | 4/2003 | Carrion et al. ................ 424/401 |
| 2007/0264345 | A1 | * | 11/2007 | Eros et al. ..................... 424/488 |

FOREIGN PATENT DOCUMENTS

WO    90/10020    9/1990

OTHER PUBLICATIONS

Lee et al., Direct Visualization of Hyaluronic Acid Polymer Gold Chain by Self-Assembled One-Dimensional Array of Nanoparticles, Macromolecules 2006, 39, 23-25 23.*
Shu et al., Disulfide Cross-Linked Hyaluronan Hydrogels Biomacromolecules 2002, 3, 1304-1311.*
Sau et al., Size controlled synthesis of gold nanoparticles using photochemically prepared seed particles, Jl. of Nanoparticle Res. 3:257-261, 2001.*
Mattson et al., A practical approach to crosslinking, Mol. Biol. Reports, 17:167-183 (1993), teaching various approaches to crosslinking.*
Brown and Jones, Hyaluronic acid: a unique topical vehicle for the localized delivery of drugs to the skin, JEADV (2005) 19, 308-318.*
Abstract, Kaur & Agrawal, Nanotechnology: A New Paradigm in Cosmeceuticals, Recent Patents on Drug Delivery & Formulation, vol. 1, No. 2, Jun. 2007, pp. 171-182.*
Guix et al., Nanoparticles for cosmetics. How safe is safe?, Contributions to Science, 4(2):213-217 (2008).*
Lee et al, Macromolecules, 2006, 39, 23-25.*
Lee et al, Biomaterials, 2008, 29, 4709-18.*
Shu et al, Biomacromolecules, 2002, 3, 1304-11.*
Lee, Hyukjin, et al., "Synthesis, characterization, and in vivo diagnostic applications of hyaluronic acid immobilized gold nanoprobes", *Biomaterials* 29 (2008), pp. 4709-4718.
Turkevich, John, et al., "A Study of the Nucleation and Growth Processes in the Synthesis of Colloidal Gold" *Discussions of the Faraday Society* 11: pp. 55-75, May 1951.

(Continued)

*Primary Examiner* — Ganapathy Krishnan
(74) *Attorney, Agent, or Firm* — Ladas & Parry LLP

(57) ABSTRACT

This invention discloses a new conjugate compound that comprises at least one HA oligomer derivatized through one thiolated linker, whereby it binds to at least one metal nanoparticle, such as, for example, a gold nanoparticle. Moreover, it discloses methods of obtaining it, as well as the use thereof in a cosmetic treatment, and cosmetic compositions that contain them.

19 Claims, 10 Drawing Sheets

(56) References Cited

OTHER PUBLICATIONS

Haiss, Wolfgang, et al., "Determination of Size and Concentration of Gold Nanoparticles from UV-Vis Spectra", *Anal Chem* 2007, 79(11), pp. 4215-4221.

Courel, Marie-Noelle, et al., "Importance of Hyaluronan Length in a Hyaladhern-Based Assay for Hyaluronan", *Analytical Biochemistry* 302, (2002), pp. 285-290.

Betrand, Philippe, et al., "Interactionof Hyaluronectin with Hyaluronic Acid Oligasaccharides", *Journal of Neurochemistry*, 45(2), 1985, pp. 434-439.

Tawada, Akira, et al., "Large-scale preparation, purification, and characterization of hyaluronan oligosaccharides from 4-mers to 52-mers", *Glycobiology*, 12(7), 2002, pp. 421-426.

Shu, Ziao Zheng, et al., "Disulfide Cross-Linked Hyaluronan Hydrogels", *Biomacromolecules* 3, 2002, pp. 1304-1311.

Lee, Haeshin, et al., "Direct Visualization of Hyaluronic Acid Polymer Chain by Self-Assembled One-Dimensional Array of Gold Nanoparticles", *Macromolecules* 39, 2006, pp. 23-25.

Kafedjiiski, Krum, et al., "Synthesis and in vitro evaluation of thiolated hyaluronic acid for mucoadhesive drug delivery", *International Journal of Pharmaceuticals* 343, 2007, pp. 48-58.

Campoccia, Davide, et al., "Semisynthetic resorbable materials from hyaluronan esterification", *Biomaterials* 19, 1998, pp. 2101-2127.

Mlcochova, Petera, et al., "Preparation and characterization of biodegradable alkylether derivatives of hyaluronan", *Carbohydrate Polymers* 69, 2007, pp. 344-352.

Widner, Bill, et al., "Hyaluronic Acid Production in *Bacillus subtilis*", *Applied and Environmental Microbiology*, Jul. 2005, pp. 3747-3752.

Deangelis, Paul L., et al., "Rapid Chemoenzymatic Synthesis of Monodisperse Hyaluronan Oligosaccharides with Immobilized Enzyme Reactors", *The Journal of Biological Chemistry*, 278 (37), 2003, pp. 35199-352003.

Jing, Wei, et al, "Synchronized Chemoenzymatic Synthesis of Monodisperse Hyaluronan Polymers", *The Journal of Biological Chemistry*, 279(4), 2004, pp. 42345-42349.

Bodevin-Authelet, Sabrina, et al., "Biosynthesis of Hyaluronan", *The Journal of Biological Chemistry*, 280(10), 2005, pp. 8813-8818.

\* cited by examiner

*thiopropionylhydrazide-HA*

CONJUGATE OF HYALURONIC ACID FOR COSMETIC TREATMENT AND PREPARATION METHOD

FIELD OF THE INVENTION

This invention relates to a new hyaluronic acid conjugate compound and a metal nanoparticle, as well as to a method of obtaining it. Moreover, the invention relates to the use thereof in cosmetic treatments.

BACKGROUND OF THE INVENTION

Hyaluronic acid, or HA, is a natural glycosaminoglycan that is very abundant in all mesodermal tissues, in the vitreous humour and in Wharton's jelly in the umbilical cord. It is present in the intercellular matrix of tissues, in the different tissues of all animal species, and has a significant role in the skin structure, being responsible for the elasticity thereof. It has the capacity to retain a large amount of water around it, thereby providing volume to the tissues.

Its structure consists of alternating disaccharide units of D-glucuronic acid and N-acetyl-D-glucosamine bound by β-1-3 and β-1-4 glycosidic bonds. Unlike other polysaccharides, HA does not have a defined shape in space, but spreads in a random manner and tends to occupy a very large volume due to the electrostatic repulsion of the carboxyl groups of glucuronic acid. At the same time, it forms meshes that retain a large amount of water.

HA has a decisive role as a connective element in tissues. The skin contains close to 56% of the HA present in the body. The body dermis has a lattice network of collagen fibres inside an interstitial substance that is largely composed of HA. This acid's elastic properties provide resistance against compression, and this is how the skin protects the underlying structures against external aggressions, whereas the non-Newtonian properties of HA allow the collagen fibres to easily move through the interstitial substance. This lubrication process by means of HA allows the skin to adapt to the changes in shape and volume that take place when the bones and ligaments move.

As we age, the quantity of HA in the skin decreases, since the skin cells progressively lose their production capacity. Furthermore, the molecular weight of HA decreases with age, such that it does not preserve water as it previously did. This decrease in volume is what causes wrinkles. It is estimated that, at the age of 40, the amount of HA in the skin has decreased by half. After the age of 60, only 10% remains.

HA has been used in cosmetics since 1996; it may be of animal origin (from hens' combs and fish's eyeballs) or of biological origin (bacterial culture extracts). HA is responsible for the elasticity of the skin. It is a great remedy against wrinkles, since it increases the volume in skin folds, grooves and depressions. The periodical application thereof causes the regeneration of the skin's own collagen. The advantage of this product is that it is a substance that is compatible with all tissues; therefore, it does not require any type of cutaneous test, as is the case with collagen.

Cosmetic treatments based on HA are well-known in the state of the art. However, the cosmetic application of HA entails the loss of the conformation of HA and, consequently, a decrease in stability and water-retaining capacity.

Therefore, the state of the art still needs to provide new HA compounds that improve the lifetime and stability of HA in order that it may be used in cosmetic treatments.

In this regard, the inventors have been surprised to discover that conjugating HA oligomers with the surface of a metal nanoparticle through a linker improves the properties of physical structure, stability and durability, and, in general, transdermal penetration properties. Therefore, the cosmetic application of this conjugate provides an effective, lasting wrinkle-filler effect on the skin, which may replace other less effective treatments.

OBJECT OF THE INVENTION

Figure 1:
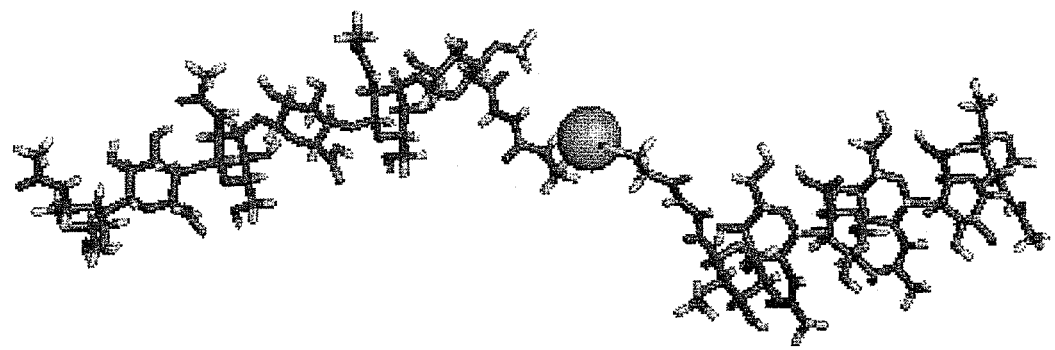
FIG. 1 represents an illustrative model of a conjugate compound of the invention, which comprises a metal nanoparticle and 2 (6-mer) oligomers of thiopropionyl hydrazide-HA, wherein each of the oligomers is derivatised through an amide chemical bond, and wherein each linker binds each HA oligomer to the metal nanoparticle.

One object of this invention relates to a new conjugate compound that comprises:
at least one metal nanoparticle; and
at least one HA oligomer derivatised through, at least, one chemical bond with at least one linker that comprises an —S— group, whereby the derivatised HA oligomer binds to the metal nanoparticle,
provided that, when the HA oligomer has a number of n monomers, and n>1,000, and the nanoparticle is a gold nanoparticle with a size of 20 nm, the linker is other than $H_2N—CH_2—CH_2—SH$.

Another object of this invention relates to various synthesis methods of obtaining the new conjugate compound.

One additional object relates to a conjugate compound that may be obtained by one of the synthesis methods of this invention.

Another additional object relates to a multi-conjugate compound that comprises:
at least one metal nanoparticle; and
at least one HA oligomer derivatised through, at least, one chemical bond with at least one linker that comprises an —S— group, whereby the derivatised HA oligomer binds to the metal nanoparticle, and
at least, one molecule that is conjugated with, at least, one metal nanoparticle.

Another additional object relates to a cosmetic composition, hereinafter cosmetic composition of the invention, that comprises at least one compound selected from:
A conjugate compound that comprises:
at least one metal nanoparticle; and
at least one HA oligomer derivatised through, at least, one chemical bond with at least one linker that comprises an —S— group, whereby the derivatised HA oligomer binds to the metal nanoparticle, and
A multi-conjugate compound of the invention,
jointly with at least one physiologically acceptable excipient.

Another additional object relates to the use of at least one compound selected from:
A conjugate compound that comprises:
at least one metal nanoparticle; and
at least one HA oligomer derivatised through, at least, one chemical bond with at least one linker that comprises an —S— group, whereby the derivatised HA oligomer binds to the metal nanoparticle, and
A multi-conjugate compound of the invention,
in the preparation of a cosmetic composition designed for topical application or for application by injection in the skin.

One additional object relates to a cosmetic treatment that comprises the topical or injected application of the cosmetic composition of this invention.

DESCRIPTION OF THE INVENTION

Therefore, in accordance with a first aspect, the invention relates to a new conjugate compound that comprises:
at least one metal nanoparticle; and
at least one HA oligomer derivatised through, at least, one chemical bond with at least one linker that comprises an —S— group, whereby the derivatised HA oligomer binds to the metal nanoparticle,
provided that, when the HA oligomer has a number of monomers n, and n>1,000, and the nanoparticle is a gold nanoparticle with a size of 20 nm, the linker is other than $H_2N—CH_2—CH_2—SH$.

In the context of the invention, the term "linker" refers to an organic molecule that covalently binds to an HA oligomer, as explained further below, and binds said HA oligomer to the metal nanoparticle. The linker in this invention contains at least one sulfur atom that binds to the metal nanoparticle. In general, the linker may have numerous different chemical structures, provided that it fulfils the function of binding the HA oligomer and the metal nanoparticle. Said structures may be variable and are easily recognised by a person skilled in the art. In a particular embodiment of the invention, the linker has one of the general formulas disclosed further below.

In this description, the term HA "monomer" refers to a unit formed by two consecutive residues of bound D-glucuronic acid and N-acetyl-D-glucosamine.

In this description, the term HA "mer" refers to a saccharide unit which may be, indistinctly, both D-glucuronic acid and N-acetyl-D-glucosamine.

The term "HA polymer" is used in this invention to refer to a natural HA oligomer, which is obtained from a natural biological source, such as, for example, those mentioned in the Background of the invention, and may be acquired from various companies that commercialise it. In some cases, it is evident that "HA polymer" and "HA oligomer" refer to the same compound, when they have the same number of monomers and the same structure; likewise, occasionally their respective derivatives, "derivatised HA polymer" and "derivatised HA oligomer", are the same. In this description, the term "HA polymer" is used for clarity purposes, to refer to the natural HA starting product that is used in the invention to obtain the conjugate or multi-conjugate compounds of the invention, in some of the methods of the invention, and has not been subject to enzymatic hydrolysis, as described further below.

In this description, terms used in the singular, such as "a", "an", "one", or "the", may in all cases refer to the singular or the plural form.

The conjugate compound may have very diverse structures, properties, and the various parameters that characterise it may vary. Amongst other parameters, it is worth mentioning the following: the size of the metal nanoparticle, which, in turn, may be a nanoparticle or a nucleus-shield particle that may comprise a metal, as described further below; the number of metal nanoparticles in the conjugate compound, which generally ranges between 1 and a maximum number that may be determined in each case by physical characterisation techniques and depends, amongst other factors, on the total number of HA oligomer linkers; the molecular weight of the HA oligomer and, therefore, the number of HA monomers; the type of linker, i.e. its chemical formula, and the number of linkers that bind the HA oligomer to the metal nanoparticle; and, depending on the linker, the type of chemical bond that covalently binds the HA oligomer to the linker, which may be an amide, an ester and an ether bond. Likewise, a conjugate compound may comprise more than one conjugated oligomer, with different numbers of monomers each.

As one may deduce from this description, the conjugate compounds defined in this invention are very numerous.

In accordance with a particular embodiment of the invention, the conjugate compound has a structure that comprises:
a) one metal nanoparticle and one or more HA oligomers, wherein each of the HA oligomers is derivatised with one linker through one chemical bond, and wherein each linker binds each HA oligomer to the metal nanoparticle (see a concrete example of this type of structure in FIG. 1).

Figure 2:
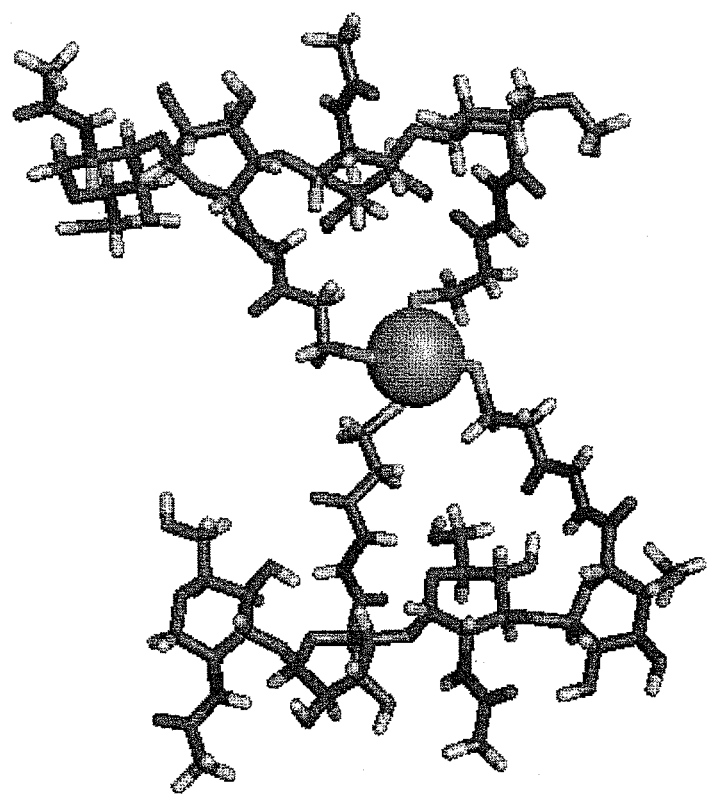
FIG. 2 represents an illustrative model of a conjugate compound that contains a metal nanoparticle and 2 (4-mer) HA oligomers, wherein each of the oligomers is derivatised in the carboxylic acid positions with two linkers, which bind each HA oligomer to the metal nanoparticle.

In another particular embodiment of the invention, the conjugate compound has a structure that comprises:

b) one metal nanoparticle and one or more HA oligomers, wherein each of the oligomers is derivatised with at least two linkers, which bind each HA oligomer to the metal nanoparticle (see a concrete example of this type of structure in FIG. 2).

Figure 3:
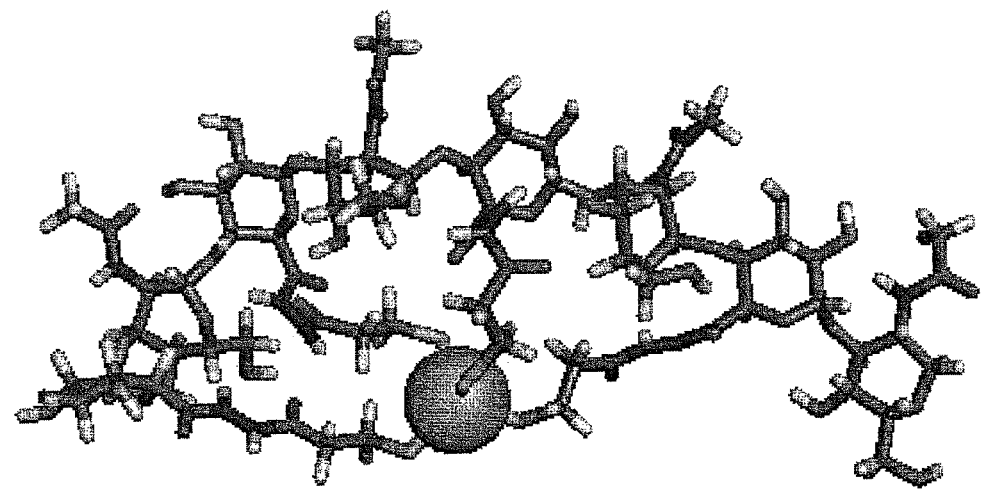
FIG. 3 represents an illustrative model of a conjugate compound that consists of 1 8-mer HA oligomer derivatised in the carboxylic acid positions through amide chemical bonds with 4 linkers, which bind the oligomer to 1 metal nanoparticle.
Figure 4:
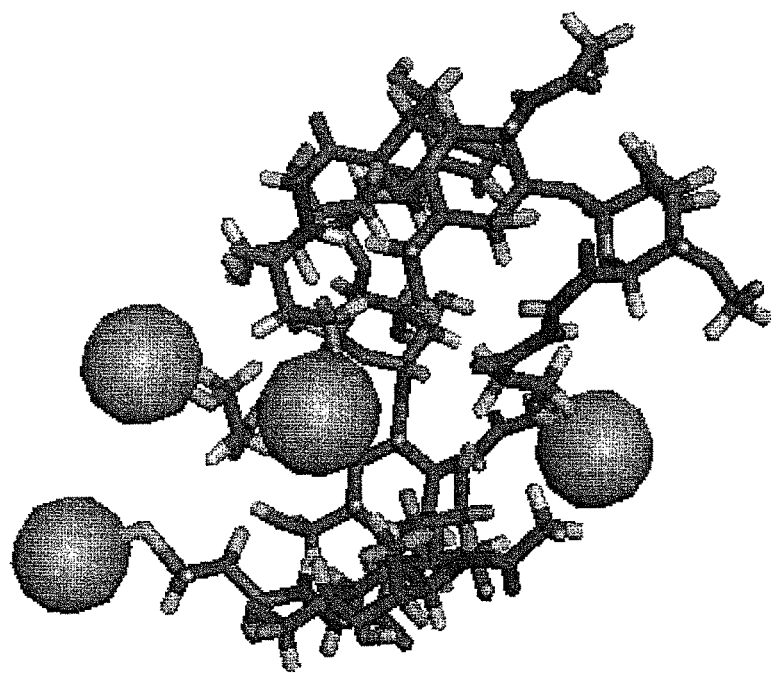
FIG. 4 represents an illustrative model of a conjugate compound that consists of 1 8-mer oligomer conjugated with 4 metal nanoparticles.

In another particular embodiment of the invention, the conjugate compound has a structure that comprises:

c) one or more HA oligomers derivatised with more than one linker each, which bind each HA oligomer to one or more metal nanoparticles (see a concrete example of this type of structure in FIG. 3 and another Example in FIG. 4).

Figure 5:
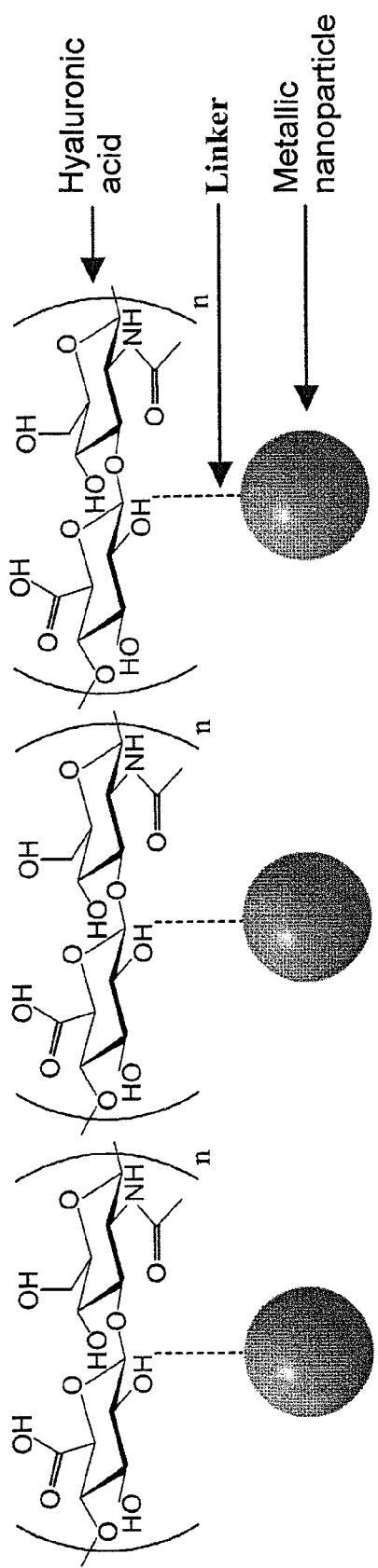
FIG. 5 shows a diagram of a conjugate compound that consists of an HA oligomer with n monomers, each bound to a metal nanoparticle by means of a linker.

FIG. 5 shows the diagram of a conjugate compound that has a structure in accordance with particular embodiment c), described above, wherein one HA oligomer has n monomers, each of them bound to one metal nanoparticle through one linker. Given that the size of the metal nanoparticle is much larger than the gap between the positions wherethrough the HA oligomer is derivatised, it is possible for the same metal nanoparticle to be conjugated with the oligomer through more than one position (FIG. 3).

The metal nanoparticle of the conjugate compound may be selected from the group formed by nanoparticles and nucleus-shield particles. The nanoparticle, the nucleus and the shield may be independently composed of a material selected from the group formed by the metals Au, Ag, Pt, Co, Fe, the oxides derived from any of the preceding metals and $TiO_2$. In a preferred embodiment, the nanoparticle is a gold nanoparticle. Both gold nanoparticles and gold nucleus-shield particles have a very versatile surface that may be functionalised with various types of biomolecules, such as HA. It is a noble element that is not very reactive in biological media.

Figure 9:
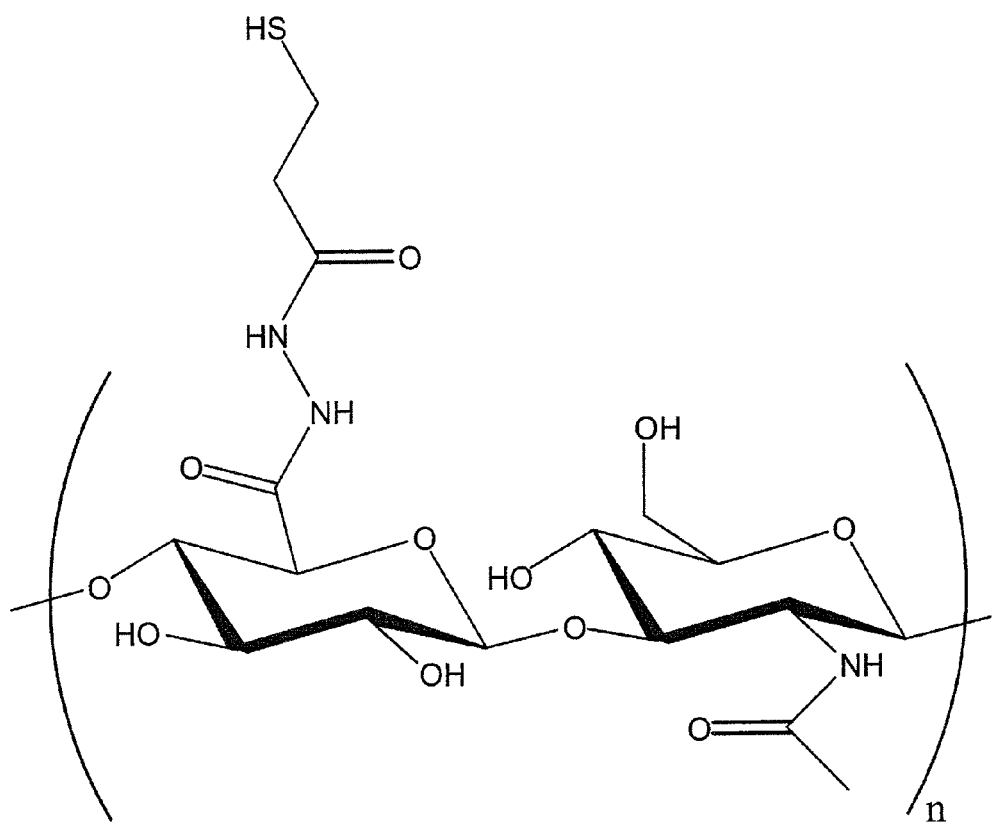
FIG. 9 diagram of a 2-mer HA oligomer of n monomers derivatised with thiopropionyl hydrazide through an amide bond.

The metal nanoparticle has a variable mean diameter size, generally ranging between 2 and 100 nm. In a preferred embodiment, the mean diameter size is between 4-50 nm. In another, more preferred embodiment, the mean diameter size is between 6-30 nm, and, in an even more preferred embodiment, the mean diameter size is between 8-15 nm.

The HA oligomer or the derivatised HA oligomer generally comprises between 1 and a maximum number of monomers, determined by the biological nature of hyaluronic acid itself. In general, this maximum number is about 50,000 HA monomers. In a particular embodiment, the hyaluronic acid oligomer comprises between 1-1,000 HA monomers; in another particular embodiment, it comprises between 1-100 HA monomers, and, in another particular embodiment, it comprises between 2-25 HA monomers. Finally, in a preferred embodiment, the derivatised HA comprises 3 monomers.

In the conjugate compound, the HA oligomer is derivatised with, at least, one linker through, at least, one covalent chemical bond that is selected from an amide, an ester and an ether bond, on the basis of the functional group of HA that is made to react in the derivatisation reaction and the formula of the linker used. In this regard, in a particular embodiment of the invention, the bond is a —CONH— amide bond, formed between a free acid group from an HA mer (glucuronic acid) and a linker with the general formula $H_2N—R_1—S—R_2$, wherein:

$R_2$ represents a group selected from
H, $—CH_3$, $—(CH_2)_n—CH_3$, $—(CH_2)_n—CH{=}CH_2$ and $—S—R_1—NH_2$ and $R_1$ represents a group selected from
$—(CH)_n—$, $—(CH)(COOH)(CH_2)_n—$, $—NH—CO—(CH_2)_n—$, where n represents an integral number between 1 and 20.

In a preferred embodiment, in the linker with the general formula $H_2N—R_1—S—R_2$, $R_2$ represents a group selected from
H, $—CH_3$, $—CH_2—CH_3$ and $—CH_2—CH{=}CH_2$ and $R_1$ represents a group selected from
$—(CH)(COOH)(CH_2)_n—$, where n is 1 or 2.

In a more preferred embodiment, the linker is thiopropionyl hydrazide, and has the formula $H_2N—NH—CO—(CH_2)_n—SH$, where n is 2. In particular, the HA oligomer already derivatised with this linker may be commercially obtained (Glycosil™, Glycosan Biosystems Inc.) and subsequently used to obtain a conjugate compound in accordance with some of the methods of this invention that are disclosed further below.

In accordance with another particular embodiment, the HA oligomer is derivatised following one of these alternatives:

a) through, at least, one —COO— ester chemical bond, formed between a carboxylic acid group from an HA mer (glucuronic acid) and a linker with the general formula $HO—R_1—S—R_2$, or b) through, at least, one —O— ether chemical bond, formed beween an —OH group of the HA oligomer and a linker with the general formula $LG\text{-}R_1—S—R_2$, where $R_2$ represents a group selected from
H, $—CH_3$, $—(CH_2)n\text{-}CH_3$, $—(CH_2)n\text{-}CH{=}CH_2$ and $—S—R_1—NH_2$ and R1 represents a group selected from
$—(CH)_n—$, $—(CH)(COOH)(CH_2)_n—$, where n represents an integral number between 1 and 20; and LG represents a leaving group.

In a preferred embodiment, in the general formulas $HO—R_1—S—R_2$ and $LG\text{-}R_1—S—R_2$, $R_2$ represents a group selected from H, $—CH_3$, $—CH_2—CH_3$ and $—CH_2—CH{=}CH_2$ and $R_1$ represents a $—(CH_2)_n—$ group, where n is a value between 1 and 20.

The conjugate compound has a ratio of number of HA mers/number of metal nanoparticles that generally ranges between 2 and 100,000. In a particular embodiment, it is between 4 and 2,000; in accordance with another particular embodiment, it is between 4 and 200; and, in accordance with another particular embodiment, it is between 4 and 50.

The number of metal nanoparticles in the conjugate compound generally ranges between 1 and a maximum number that may be determined by physical characterisation techniques, and which depends on various factors, such as the total number of linkers in the HA oligomer.

In a particular embodiment, the conjugate compound is obtained in accordance with the method described in Example 1. The conjugate compound has been visualised by Transmission Electron Microscopy (TEM) (FIG. 6). The gold nanoparticles have optical properties due to the surface resonance plasmon; thus, it is possible to precisely measure the general adsorption of molecules to the surface of the metal.

The TEM image shows that the gold nanoparticles concentrate in separate, disperse groups. FIG. 7 shows the UV-Vis Spectrum of the gold nanoparticles stabilised with sodium citrate, and how conjugation of the HA oligomers derivatised thereto induces a displacement of the absorption peak to a higher wavelength, in this case 522 nm, as compared to that of the non-conjugated gold nanoparticles (519 nm). FIG. 8 shows the Z potential, and we may observe that conjugation of the derivatised HA oligomers induces a displacement of the Z potential peak to −19.1 mV, as compared to the −50.8-mV peak corresponding to the non-conjugated gold nanoparticles.

As previously mentioned, in accordance with a particular embodiment, the conjugate compound is that which has a general structure like the one represented in FIG. 5. In a more particular case, the conjugate compound comprises gold nanoparticles of approximately 8 nm, and one derivatised HA oligomer, the formula whereof is shown in FIG. 9, "thiopropionyl hydrazide-HA". This conjugate compound is obtained in accordance with the method described in Example 3 and has been characterised.

Figure 10:
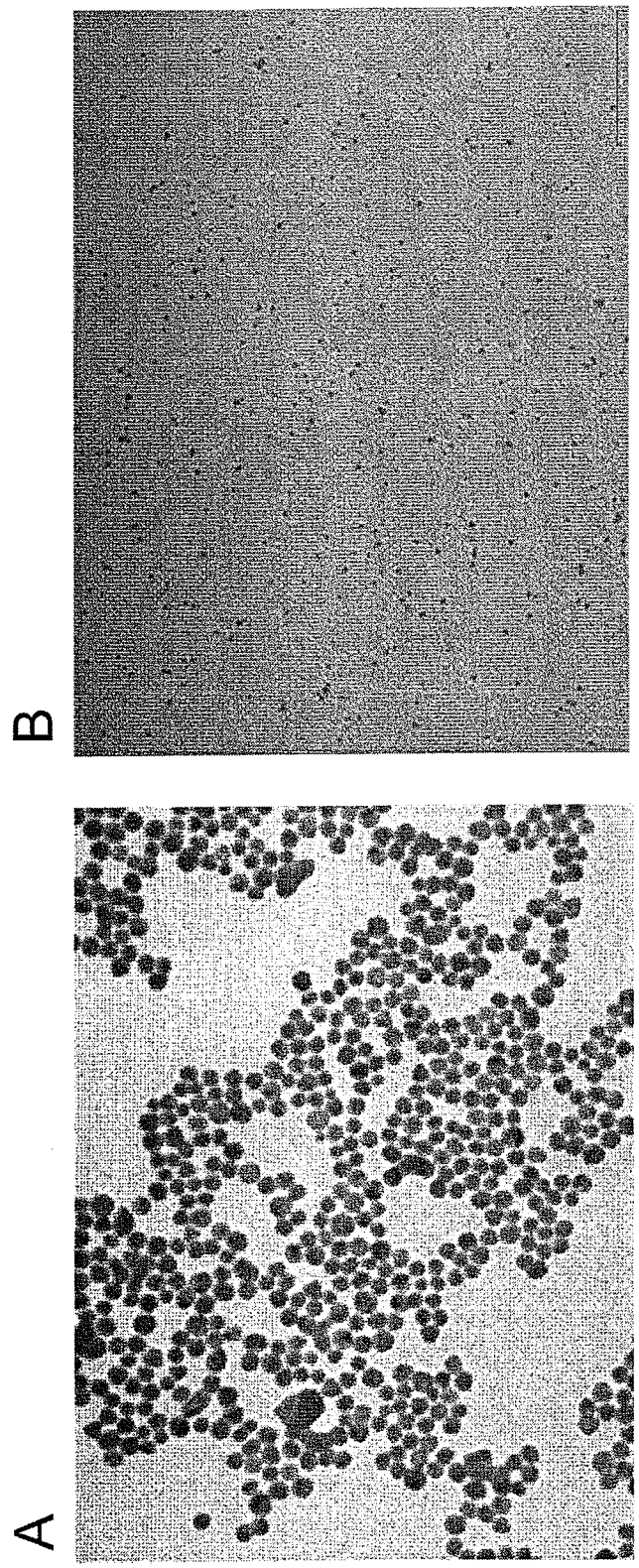
FIG. 10 transmission electron microscopy (TEM) images of the conjugate compound obtained in Example 3, captured with a Hitachi H-7000 transmission electron microscope with an acceleration voltage of 75 kV.

In this regard, the conjugate compound has been visualised by Transmission Electron Microscopy (TEM). FIG. 10-A shows that the gold nanoparticles that are not conjugated with HA tend to arrange themselves in characteristic groupings, where the distance between the nanoparticles is the minimum possible one due to their stabilisation with sodium citrate.

On the other hand, when the gold nanoparticles are conjugated with HA (FIG. 10-B), it is observed that they are farther apart and the initial characteristic grouping of the non-conjugated nanoparticles is lost. In this case, it is suspected that the gold nanoparticles are grouped along the HA oligomer chains, which, in turn, intertwine (cross-linking effect) to form a mesh of the conjugate compound.

Figure 11:
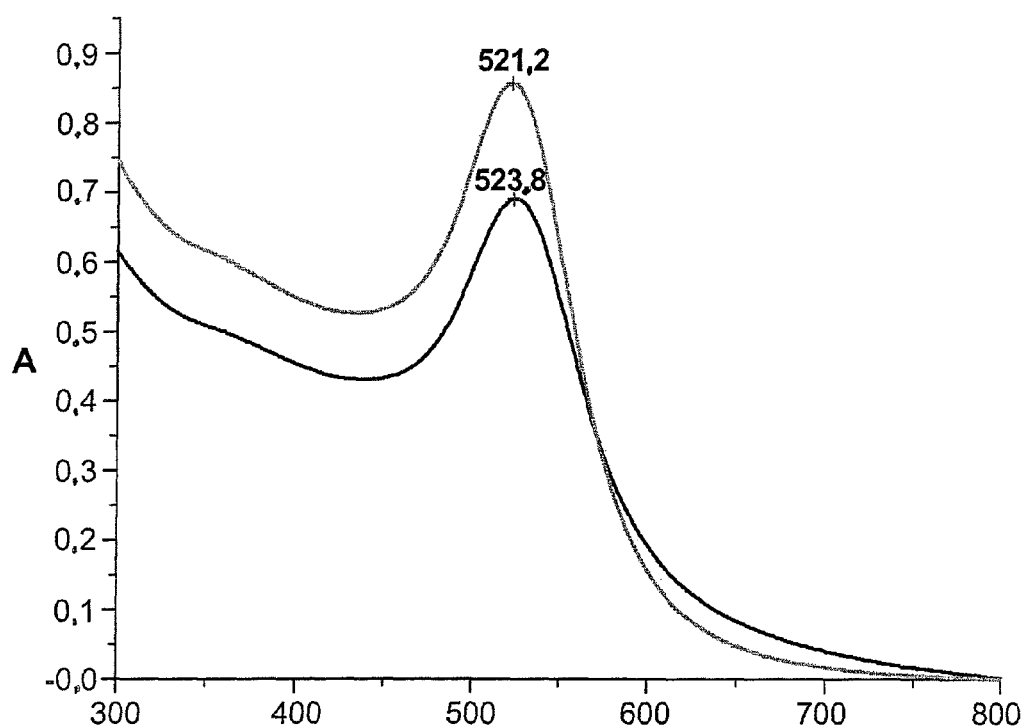
FIG. 11: UV-Vis absorption spectra of a solution of gold nanoparticles and a conjugate compound in accordance with the invention (Example 3), recorded with a Shimadzu UV-240IPC spectroscope. A represents the absorbance and A represents the wavelength (nm).

In this particular embodiment, the gold nanoparticles stabilised with sodium citrate show a peak at 521.2 nm (approx.). However, when they are conjugated with derivatised HA oligomers, one may observe a displacement of the absorption peak to a higher wavelength, in this case 523.8 nm (FIG. 11).

The conjugate compound has great stability and resistance to be absorbed by the organism due to its conjugation with the metal nanoparticles. As a consequence, HA preserves its great water-retention capacity. Furthermore, although the inventors do not wish to be bound by any theory, it seems that the metal nanoparticle might act as an inhibitor of the activity of the enzyme hyaluronidase on HA, which might also have an additional effect on the durability of the properties of HA.

In accordance with another aspect, the invention relates to methods of preparing a conjugate compound that comprises:

at least one metal nanoparticle; and at least one HA oligomer derivatised through, at least, one chemical bond with at least one linker that comprises an —S— group, whereby the derivatised HA oligomer binds to the metal nanoparticle, provided that, when the HA oligomer has a number of monomers n, and n>1,000, and the nanoparticle is a gold nanoparticle with a size of 20 nm, the linker is other than $H_2N-CH_2-CH_2-SH$.

Preparation of the conjugate compounds may be performed in accordance with one or more of the methods described below, all of which are objects of this invention.

The methods described below comprise a common step, the preparation of a metal nanoparticle, which is performed, with shape and size control, by means of chemical reactions that are well known to those skilled in the art. In a particular embodiment, gold nanoparticles are prepared, and the method used to do so is based on synthetic methods that are broadly described in the literature, such as the so-called sodium citrate method (Turkevich, J., P. C. Stevenson, et al. (1951). "[The nucleation and growth processes in the synthesis of colloidal gold]." Discussions of the Faraday Society 11: 55-75), or by reduction with NaBH4 (Haiss, W., N. T. Thanh, et al. (2007). "Determination of size and concentration of gold nanoparticles from UV-vis spectra." Anal Chem 79(11): 4215-21).

The different methods are described below:

Method A) comprises the following steps:

(i) enzymatic hydrolysis of an HA polymer;

(ii) obtainment of the HA oligomer fragments;

(iii) derivatisation of the HA oligomer fragments by chemical reaction with a linker that comprises an —S— group, through at least one amide, ester or ether chemical bond; and (iv) conjugation of at least one derivatised HA oligomer fragment obtained in the preceding step with at least one metal nanoparticle.

Method B) comprises the following steps:

(i) derivatisation of an HA polymer by chemical reaction with a linker that comprises an —S— group, by the formation of at least one amide, ester or ether chemical bond;

(ii) enzymatic hydrolysis of the derivatised HA polymer;

(iii) obtainment of derivatised HA oligomer fragments; and (iv) conjugation of at least one of the fragments obtained in the preceding step with at least one metal nanoparticle.

Method C) comprises the following steps:

(i) derivatisation of an HA polymer by chemical reaction with a linker that comprises an —S— group through at least one amide, ester or ether chemical bond; and (ii) conjugation of the derivatised HA polymer obtained in the preceding step with at least one metal nanoparticle;

(iii) enzymatic hydrolysis of the derivatised HA polymer;

(iv) obtainment of the conjugate compound.

In accordance with Method A, step (ii) consists of the enzymatic hydrolysis of an HA polymer. The starting HA polymer is commercially obtained, as previously mentioned. In turn, the HA polymer comprises oligomers with different numbers of HA mers, which are hydrolysed to produce oligosaccharide fragments (oligomer fragments) of a smaller size, and with a variable structure, by the action of two types of possible enzymes a) and b), as shown in Diagram 1:

a) Hydrolysis with a hyaluronidase (hyaluronate 4-glucanohydrolase, E.C. 3.2.1.35). Hydrolysis takes place in bonds β-1-3 of the HA polymer and results in structures of the type D-GlcA-(1→3)[D-GlcNAc-(1→4)-D-GlcA]n-D-GlcNAc, with a saturated uronic acid at the hydrolysed end. The oligosaccharides are prepared by the digestion of HA polymer with BTH ("Bovine Testicular Hyaluronidase") (30 U/mg HA) at 37° C. with different reaction times, as described in the literature (Bertrand, P. and B. Delpech (1985), "Interaction of hyaluronectin with hyaluronic acid oligosaccharides." J Neurochem 45(2): 434-9; Courel, M. N., C. Maingonnat, et al. (2002). "Importance of hyaluronan length in a hyaladherin-based assay for hyaluronan." Anal Biochem 302(2): 285-90.; Tawada, A., T. Masa, et al. (2002). "Large-scale preparation, purification, and characterization of hyaluronan oligosaccharides from 4-mers to 52-mers." Glycobiology 12(7): 421-6). The size of the final oligosaccharide varies depending on the incubation time.

b) Hydrolysis with a hyaluronate lyase (E.C. 4.2.2.1). Hydrolysis takes place in bonds β-1-4, and oligosaccharides are obtained with a Δ4-unsaturated uronic acid at the hydrolysed end, to produce oligosaccharides with structures L-4dthrHex4enA-(1→3)-[D-GlcNAc-(1→4)-D-GlcA]n-(1→3)-D-GlcNAc.

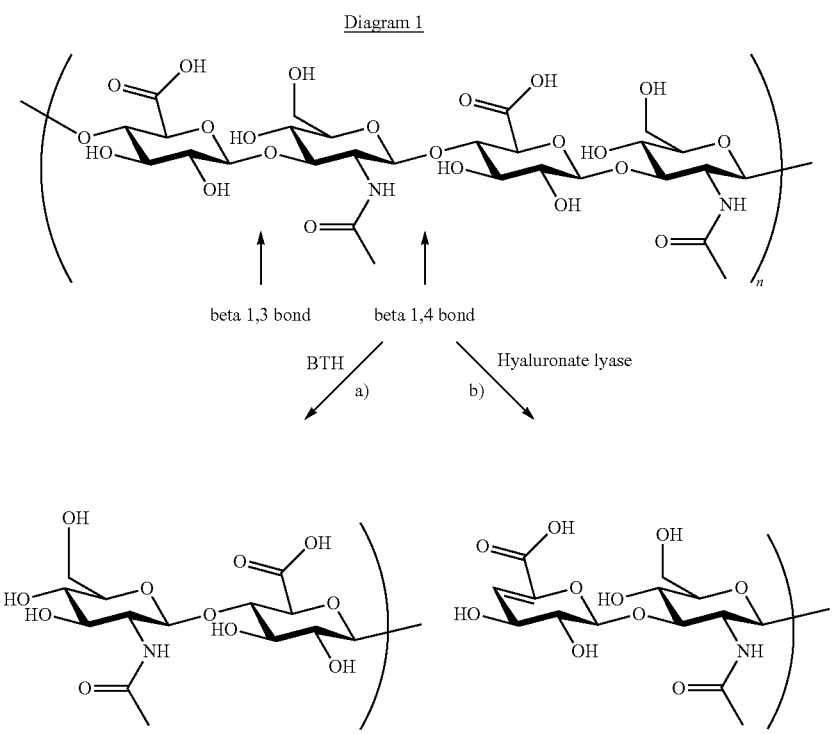

Diagram 1

Subsequently, in method A, step (ii) takes place, wherein the oligomer fragments of different sizes resulting from the enzymatic degradation are optionally purified by means of a number of conventional techniques, such as centrifugation, chromatographies, desalting and lyophilisation. Subsequently, the purified oligomer fragments are derivatised (iii) by chemical reaction with a linker. The derivatisation thereof is performed by the modification of one of the two following types of functional groups: carboxylic acid groups (COOH) or alcohols (OH), both primary and secondary, of the disaccharide unit marked in Diagram 2:

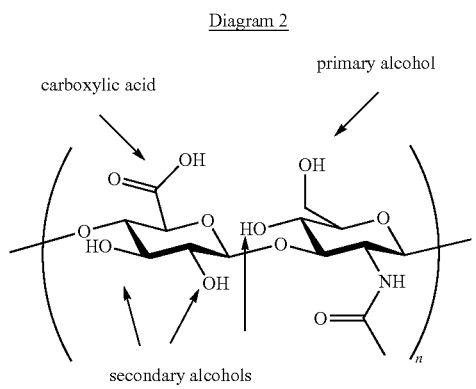

Diagram 2

The carboxylic acid groups (COOH) of glucuronic acid present throughout the HA oligomer may be derivatised with a linker by the formation of two types of bonds, as shown in Diagram 3:

1) By the formation of an amide bond (using the carbodiimide activation method) with a linker that contains an amine group with the general formula:

$H_2N-R_1-S-R_2$, where $R_2$ represents a group selected from
H, $-CH_3$, $-(CH_2)_n-CH_3$, $-(CH_2)_n-CH=CH_2$ and $-S-R_1-NH_2$ and $R_1$ represents a group selected from
$-(CH)_n-$, $-(CH)(COOH)(CH_2)_n-$, $-NH-CO-(CH_2)_n-$, where n represents an integral number between 1 and 20;

See examples in the following documents: (Shu, X. Z., Y. Liu, et al. (2002). "Disulfide cross-linked hyaluronan hydrogels." Biomacromolecules 3(6): 1304-11; Lee, H., S.-H. Choi, et al. (2006). "Direct Visualization of Hyaluronic Acid Polymer Chain by Self-Assembled One-Dimensional Array of Gold Nanoparticles." Macromolecules 39(1): 23-25; Kafedjiiski, K., R. K. Jetti, et al. (2007). "Synthesis and in vitro evaluation of thiolated hyaluronic acid for mucoadhesive drug delivery." Int J Pharm 343(1-2): 48-58).

2) By an esterificaction reaction, using a linker that comprises an alcohol group with the general formula:

$HO-R_1-S-R_2$, where $R_2$ represents a group selected from
H, $-CH_3$, $-(CH_2)_n-CH_3$, $-(CH2)_n-CH=CH_2$ and $-S-R_1-NH_2$ and $R_1$ represents a group selected from
$-(CH)_n-$, $-(CH)(COOH)(CH_2)_n-$, where n is a value between 1 and 20;

(See examples) (Campoccia, D., P. Doherty, et al. (1998). "Semisynthetic resorbable materials from hyaluronan esterification." Biomaterials 19(23): 2101-27).

Diagram 3

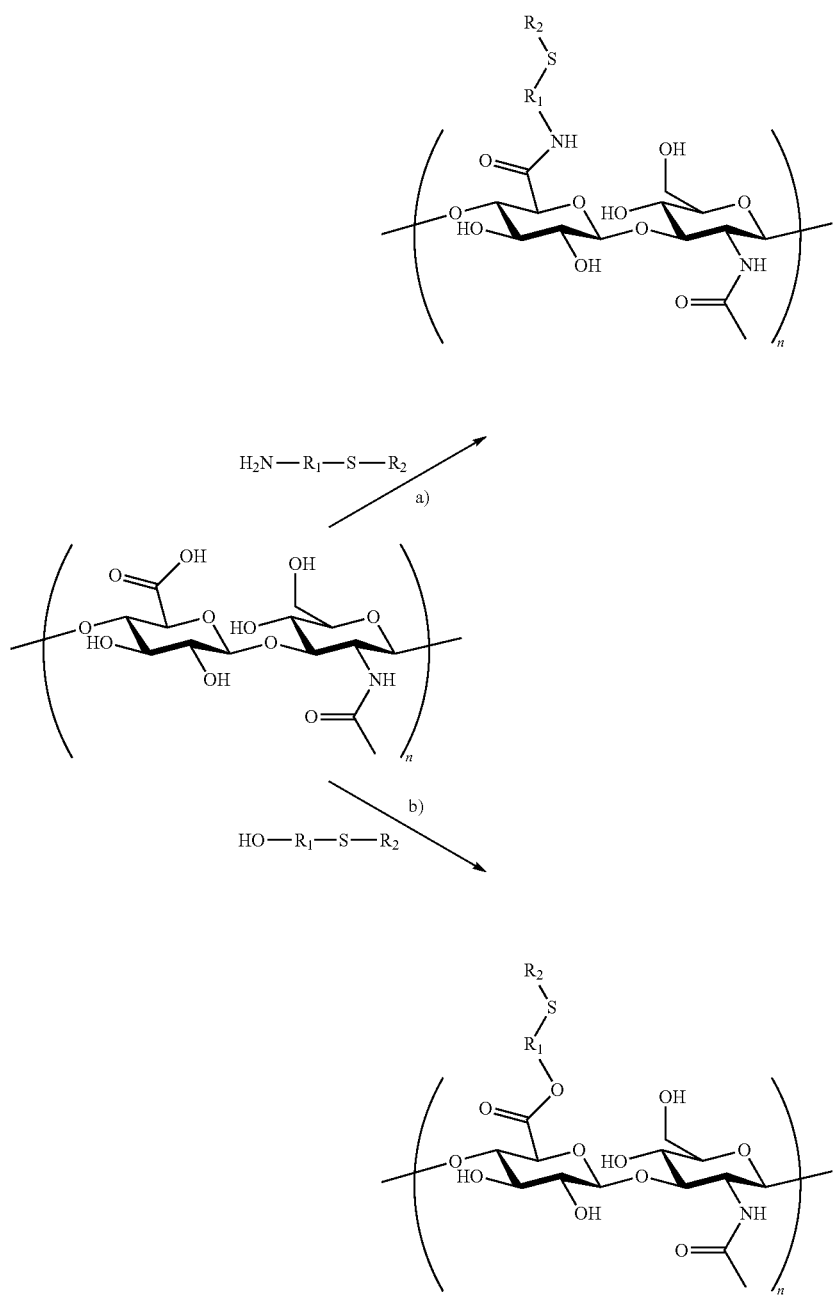

The alcohols (OH), both primary and secondary, of the disaccharide unit (Diagram 2) may be derivatised with a linker with the general formula:

LG-R$_1$—S—R$_2$, where

R$_2$ represents a group selected from
H, —CH$_3$, —(CH$_2$)$_n$—CH$_3$, —(CH$_2$)$_n$—CH=CH$_2$ and —S—R$_1$—NH$_2$ and R$_1$ represents a group selected from
—(CH)$_n$—, —(CH)(COOH)(CH$_2$)$_n$—, where n represents an integral number between 1 and 20; and LG represents a leaving group by the formation of ether-type bonds, as shown in Diagram 4. (See examples in: Micochova, P., V. Hajkova, et al. (2007). "Preparation and characterization of biodegradable alkylether derivatives of hyaluronan." Carbohydrate Polymers 69(2): 344-352)

By varying the reaction conditions, such as the proportion of the reagents, the quantity and/or type of solvent, the pH, the temperature and the reaction time, one may control that the primary alcohol, as opposed to the secondary alcohols, is mostly functionalised, as well as the amount of mono-, di- or tri-substitution of the secondary alcohols.

Diagram 4

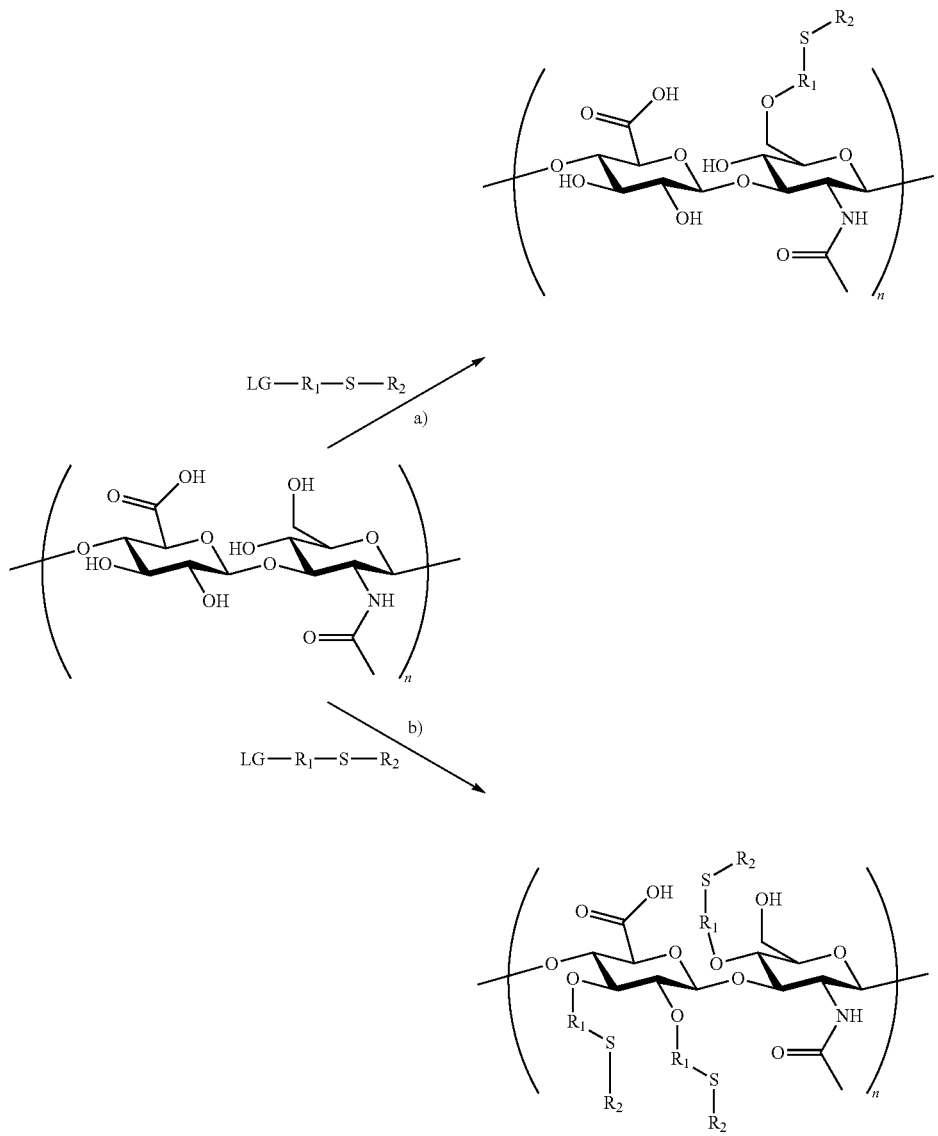

Likewise, in the case of the different oligomer fragments resulting from the enzymatic degradation with Hyaluronidase, an additional secondary alcohol appears, located at the hydrolysed end of the terminal disaccharide unit, which is also prone to being derivatised under similar conditions to those of the other secondary alcohols, as shown in the following Diagram 5:

Diagram 5

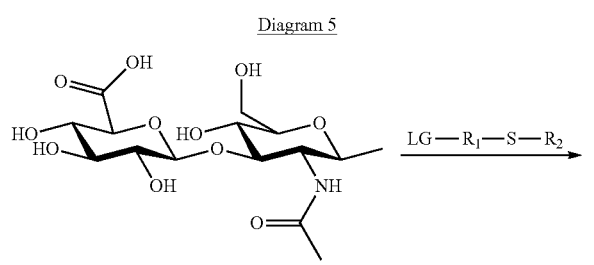

-continued

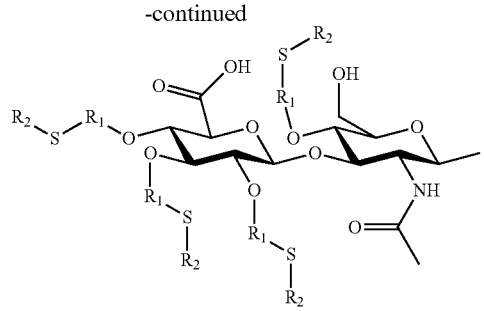

In step (iv) of method A, least one of the derivatised HA oligomer fragments is conjugated with, at least, one metal nanoparticle. To perform the conjugation reaction, an aqueous solution with a concentration generally of about 1012 metal nanoparticles per milliliter is typically stirred in the presence of a large excess of the derivatised HA oligomer in question, at ambient temperature for 1 hour. The proportion of HA oligomer with respect to the concentration of metal nanoparticles is calculated in the following manner: a) the number of metal atoms on the surface of a sphere is calculated by theoretically calculating the surface area thereof, and assuming that each atom occupies 1-2 nm$^2$. It is assumed that each sulfur atom in the linker is conjugated with a single atom of the metal nanoparticle. Taking into consideration the number of metal nanoparticles in the solution, an excess of 100 times more derivatised HA oligomer is added.

The conjugate compound obtained is purified and subsequently isolated by dialysis, in accordance with the methodology described in example 2.1.4.

Methods B) and C) of the invention are easily performed by a person skilled in the art, by modifying the order of reaction steps (i) to (iv) of method A), in view of the content of this description and the knowledge of the person skilled in the art.

Another additonal method of obtaining a conjugate compound is method D), which comprises:
(i) enzymatic hydrolysis of a derivatised HA polymer with one linker that comprises an —S— group, through at least one amide, ester or ether chemical bond;
(ii) obtainment of the derivatised HA oligomer fragments; and
(iii) conjugation of at least one derivatised HA oligomer fragment obtained in the preceding step with at least one metal nanoparticle.

Method E) of preparing a conjugate compound comprises:
(i) conjugation of a derivatised HA polymer with one linker that comprises an —S— group, through at least one amide, ester or ether chemical bond, with at least one metal nanoparticle;
(ii) enzymatic hydrolysis of the product resulting from the preceding step; and
(iii) obtainment of the conjugate compound.

In a preferred embodiment of both method D) and method E) of this invention, the starting point is a previously derivatised HA polymer, commercially obtainable, such as, for example, Glycosil™ (Glycosan Biosystems Inc., see Example 1). Glycosil™ may, therefore, be conjugated with a metal nanoparticle in the first place, and, subsequently, be hydrolysed to generate derivatised HA oligomer fragments already bound to the metal nanoparticle (method E). Alternatively, Glycosil™ may be first hydrolysed to generate derivatised HA oligomer fragments which are subsequently conjugated with a metal nanoparticle (method D).

In accordance with method F) of obtaining a conjugate compound, HA oligomers of up to 1,000 kDa are obtained by biosynthesis, by the action of a Hyaluronate Synthase, in the conventional manner, as described in the state of the art. See the examples in: APPLIED AND ENVIRONMENTAL MICROBIOLOGY, 2005, 71, No. 7, p. 3747-3752; JOURNAL OF BIOLOGICAL CHEMISTRY Vol. 278, No. 37, pp. 35199-35203, 2003; JOURNAL OF BIOLOGICAL CHEMISTRY Vol. 279, No. 40, pp. 42345-42349, 2004; JOURNAL OF BIOLOGICAL CHEMISTRY Vol. 280, No. 10, pp. 8813-8818, 2005). Following the biosynthesis of the HA oligomers, these are derivatised by any of the methods and linkers described in this invention. Finally, the derivatised HA oligomers are conjugated with, at least, one metal nanoparticle in accordance with the methodology described in this invention.

In accordance with a particular embodiment, the biosynthesised HA oligomers of up to 1,000 kDa are derivatised through the —OH group of position 3 or 4 of the oligomer's initial or final saccharide with one linker with the general formula LG-R$_1$—S—R$_2$.

Finally, a conjugate compound may be prepared by method G, which comprises:
at least one metal nanoparticle; and
at least one HA polymer or oligomer derivatised through, at least, one chemical bond with at least one linker that comprises an —S— group, whereby the derivatised HA oligomer binds to the metal nanoparticle,
provided that, when the HA polymer or oligomer has a number of monomers n, and n>1,000, and the nanoparticle is a gold nanoparticle with a size of 20 nm, the linker is other than H$_2$N—CH$_2$—CH$_2$—SH.

Method G comprises the following steps:
(i) starting from an HA polymer or oligomer,
(ii) derivatising it with at least one linker that comprises an —S— group through at least one amide, ester or ether chemical bond;
(iii) conjugating a derivatised HA polymer or oligomer with one or more metal nanoparticles, and
(iv) obtaining the conjugate compound.

Method G is characterised by the absence of an enzymatic hydrolysis step. The starting HA polymer or oligomer for method G is obtained from any biological source of HA, from various companies that commercialise them. The derivatisation is performed by the modification of one of the two types of functional groups: the carboxylic acid groups (COOH) or the alcohols (OH), both primary and secondary, in accordance with any of the methods described above. Subsequently, the conjugation step is performed, following the already described methodology.

In an additional aspect, the invention relates to a conjugate compound that may be obtained by, at least, one of the methods described above. The various conjugate compounds may be easily obtained by a person skilled in the art in view of the content of this description, the Examples and common general knowledge, by changing the parameters described above, such as, for example, the size of the metal nanoparticles used, the oligomers, the type of linker, as well as the reaction conditions.

In another additional aspect, the invention relates to a multi-conjugate compound, hereinafter multi-conjugate compound of the invention, that comprises:
at least one metal nanoparticle; and
at least one HA oligomer derivatised through, at least, one chemical bond with at least one linker that comprises an —S— group, whereby the derivatised HA molecule binds to the metal nanoparticle, and
at least, one molecule conjugated with, at least, one metal nanoparticle.

Amongst the different molecules that may be used in this invention, it is worth mentioning, for example and amongst others, a peptide, a protein, an HA hydrolysis inhibitor. In a particular embodiment of the invention, said molecule is a compound selected from the group formed by the HA hydrolysis inhibitors produced by an enzyme from the hyaluronidase family.

The multi-conjugate compound of the invention, which additionally comprises another additional conjugated molecule, may be easily obtained by techniques of molecule multi-conjugation with the surface of a metal nanoparticle known by those skilled in the art. Each molecule to be conjugated with the metal nanoparticle is previously derivatised with a given linker. Multi-conjugation techniques are based on the difference in affinity of the linker wherethrough each type of molecule has been derivatised and the difference in concentration of each type of molecule in the conjugation reaction with the metal nanoparticle.

In another additional aspect, the invention relates to a cosmetic composition that comprises at least one compound selected from:
- a conjugate compound that comprises:
  - at least one metal nanoparticle; and
  - at least one HA oligomer derivatised through, at least, one chemical bond with at least one linker that comprises an —S— group, whereby the derivatised HA oligomer binds to the metal nanoparticle, or
- a multi-conjugate compound of the invention, together with at least one physiologically acceptable excipient. Said excipients may be easily selected by a person skilled in the art, on the basis, amongst other aspects, of the properties and characteristics of the specific conjugate compound. The cosmetic composition may be prepared for topical application or for application by injection.

In another additional aspect, the invention relates to the use of at least one compound selected from:
- a conjugate compound that comprises:
  - at least one metal nanoparticle; and
  - at least one HA oligomer derivatised through, at least, one chemical bond with at least one linker that comprises an —S— group, whereby one derivatised HA oligomer binds to the metal nanoparticle, or
- a multi-conjugate compound of the invention, in the preparation of a cosmetic composition, in particular for topical application or for application by injection in the skin.

Therefore, another additional aspect of the invention relates to a cosmetic treatment of the skin of a human being, which comprises the application of the cosmetic composition of this invention.

The cosmetic treatment exhibits advantages with respect to the HA-based cosmetic treatments in the state of the art in that it improves the physical structure and stability of HA. The conjugate compound absorbs water in the deep layers of the skin, thereby creating the necessary filler effect to diminish wrinkles and folds.

The binding of the HA oligomer to the metal nanoparticle seems to protect the HA oligomers from direct absorption by the organism and makes it possible to supply HA at large concentrations, since a single conjugate compound concentrates several HA oligomers. Without wishing to bind themselves to any theory, the inventors consider that the mechanisms whereby the conjugation with a metal nanoparticle protects HA from being absorbed could be the following:

On the one hand, the structure of the HA oligomers that coat the metal nanoparticle has a spatial distribution that is less reactive toward the absorption metabolism.

On the other hand, the competition between the bond, through a linker, of the HA oligomer-metal nanoparticle, with respect to reactions that would degrade it displaces the biochemical equilibrium, thereby prolonging the half-life of HA.

Finally, in the case of oligomers conjugated with a metal nanoparticle at several positions, a cross-linking effect is obtained due to the distribution of the oligomer on the surface of the metal nanoparticle, since it has bound thereto at several positions. This could further hinder the action of hyaluronidase, consequently increasing the stability and durability of HA.

Again, and without wishing to bind themselves to any theory, the inventors believe that it is possible that, when the oligomer is exposed to enzymatic degradation (normally hyaluronidase), the conjugate compound could chemically protect the parts of HA that are prone to being degraded by the enzyme activity, since the metal nanoparticle is conjugated at a structural site close to the functional group wherethrough said enzyme fragments the oligomer. Thus, the action of hyaluronidase on the HA oligomer would be hindered.

In a particular embodiment, the cosmetic treatment is topical, and exhibits, amongst other advantages, the fact that it is accessible to all persons, in the sense that they themselves may implement it on the skin without any risk whatsoever, it is painless, comfortable and economically more affordable than a treatment by injection. The conjugate or multi-conjugate compound designed for topical application comprises, preferably, HA oligomers with a molecular weight below 1,000 kDa, which may easily penetrate to the dermis. In this way, the conjugated HA oligomer absorbs water in the deep layers of the skin, with the necessary filler effect to diminish wrinkles and folds.

In another particular embodiment, the cosmetic treatment is by injection and also exhibits some advantages. In this regard, whereas current treatments maintain their effectiveness for between 4 and 6 months, after which the filler effect disappears, the conjugation of HA oligomers with nanoparticles improves the stability of the HA oligomer, resulting in a product that maintains its wrinkle- and fold-correction effect for a longer period of time, making it possible to space out the need for injected treatments and thereby improving the users' quality of life. In a particular embodiment, the conjugate or multi-conjugate compound designed for application by injection comprises, preferably, HA oligomers with a molecular weight greater than 500 kDa, since, once injected in the deep layers of the skin, they have greater durability.

Below we show illustrative examples of this invention, which are presented in order to facilitate understanding of the invention and may in no case be considered to be a limitation of the scope thereof.

EXAMPLES

Example 1

Obtainment of a Conjugate Compound

Example 1.1

Synthesis of Gold Nanoparticles

An aqueous solution (150 ml) of sodium citrate (2.2 mM) was heated to boiling under vigorous stirring. The next step consisted of adding 1 ml of an aqueous solution (23.4 mM) of HAuCl4 to the boiling solution. The reduction took place in approximately 2 minutes and a gold nanoparticle solution was formed, which underwent an indicative change of colour from purplish to intense red. Finally, the reactor was separated from the heat source and allowed to cool to ambient temperature. The gold nanoparticles thus obtained were characterised by UV-Vis. The mean size of the gold nanoparticles, 8 nm, was determined by computer processing of the images obtained by TEM; the diameter of a random sample of nanoparticles was also measured and the Gaussian size distribution was performed.

Example 1.2

Functionalisation of Gold Nanoparticles with Derivatised HA Oligomer (21-Monomers)

1.2.1 Enzymatic Hydrolysis of Thiopropionyl Hydrazide-HA (Derivatised HA Polymer)

Thiopropionyl hydrazide-HA (Glycosil™, Glycosan Biosystems Inc.) was depolimerised by the action of the enzyme hyaluronate 4-glucanohydrolase ("Bovine Testicular Hyaluronidase (BTH)") (E.C. 3.2.1.35) (Hyaluronidase Type I-S, Sigma-Aldrich). 5*104 U of BTH were added to a solution containing 5 mg of oligomers of thiopropionyl hydrazide-HA in 25 ml of aqueous buffer solution (100 mM sodium phosphate, 150 mM sodium chloride, pH 5.3) and left to incubate for 40 hours at 37° C. The enzymatic reaction was stopped by boiling the sample for 20 min. (Glycobiology, July 2002; 12(7):421-6).

1.2.2 Purification of the Derivatised HA Oligomers

The mixture of derivatised HA oligomers was centrifuged at 10,000 rpm for 30 min and the supernatant was concentrated and lyophilised. Subsequently, the lyophilised sample was reconstituted in distilled water. (Glycobiology, July 2002; 12(7):421-6).

Example 1.3

Conjugation of Gold Nanoparticles with Derivatised HA Oligomers (21-monomers)

The 8-nm gold nanoparticles obtained in accordance with Example 1.1 were functionalised with the derivatised oligomers (thiopropionyl hydrazide-HA, MW 1,455 g/mol) obtained in the preceding step, by the addition of 100 µl of a 1.5 mM solution of derivatised oligomer per 5 ml of gold nanoparticle solution. The reaction was performed at ambient temperature and under magnetic stirring for 30 minutes. The reaction was stopped by decreasing the temperature (inside the refrigerator). The purification was performed by dialysis (molecular weight cut-off (MWCO) 16 mm) against sodium citrate (2.3 mM, 3.25 g/5 l H2O). The conjugate compound was obtained.

Example 1.4

Characterisation of the Conjugate Compound Obtained 1.4.1 UV-Vis Spectrum

Figure 7:
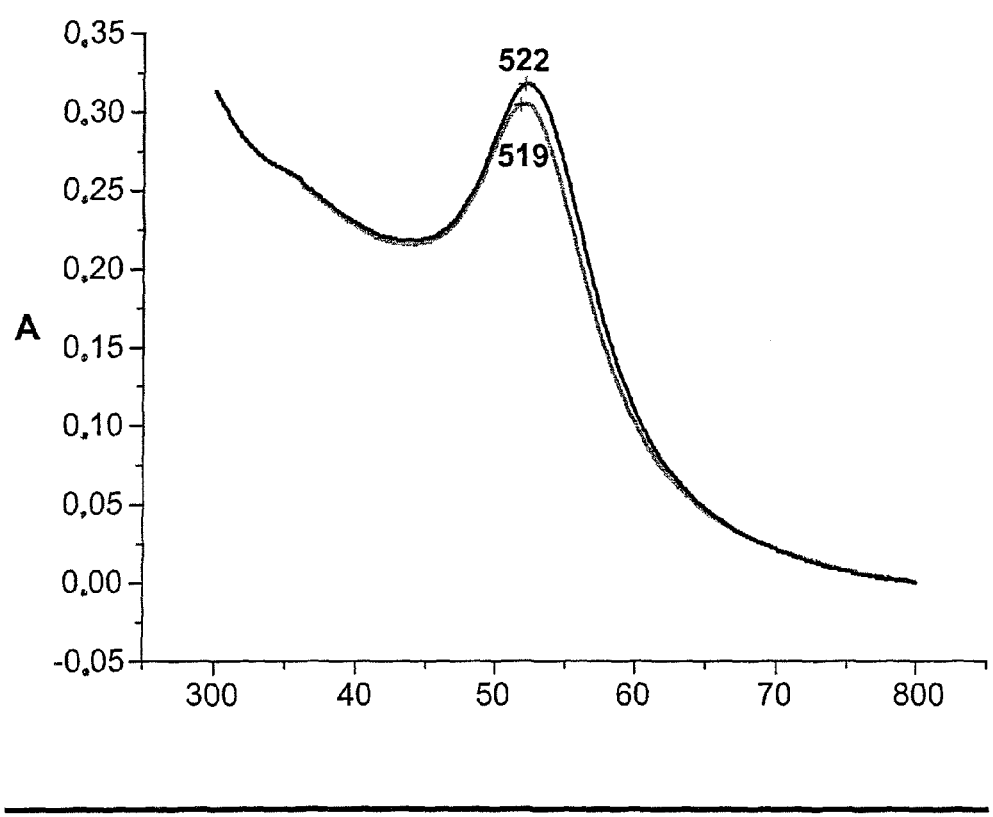
FIG. 7 UV-Vis absorption spectra of a solution of gold nanoparticles and the conjugate compound obtained in Example 1, recorded with a Shimadzu UV-240IPC spectroscope. A represents the absorbance and A represents the wavelength (nm).

The UV-Vis absorption spectra of the purified conjugate compound solution obtained in the preceding step were recorded. The conjugation of the derivatised HA oligomers with a nanoparticle induces a displacement of the absorption peak to a higher wavelength (in this case 522 nm), as shown in FIG. 7, as compared to the absorption peak of the non-conjugated gold nanoparticles (519 nm).

1.4.2 Visualisation of the Conjugate Compound by Transmission Electron Microscopy (TEM)

Figure 6:
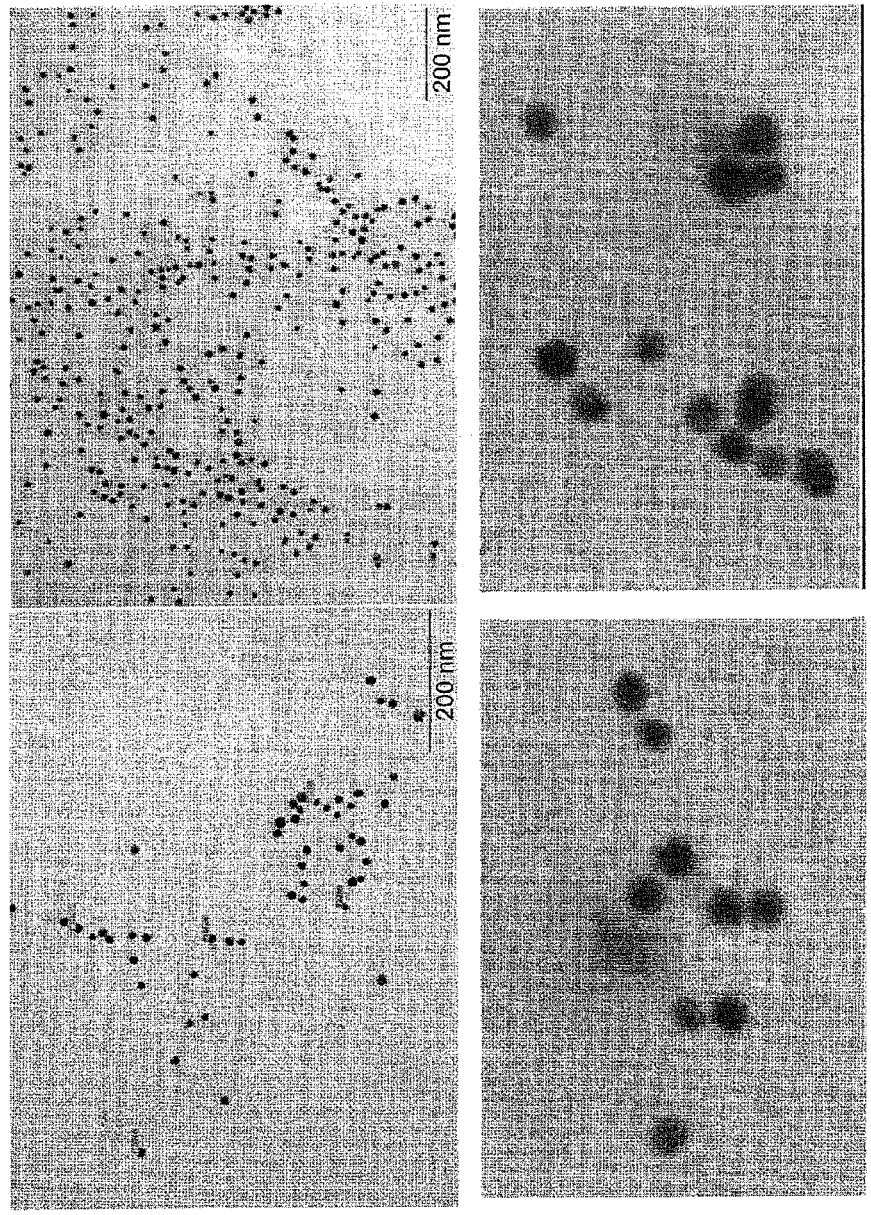
FIG. 6 transmission electron microscopy (TEM) images of the conjugate compound obtained in Example 1, captured with a Hitachi H-7000 transmission electron microscope with an acceleration voltage of 75 kV.

The TEM images of the conjugate compound (FIG. 6) obtained were captured. The samples for the TEM studies were prepared by depositing a drop of the aqueous solution of the purified conjugate compound obtained on TEM grids coated with a carbon membrane.

1.4.3 Z Potential Spectrum of the Conjugate Compound

Figure 8:
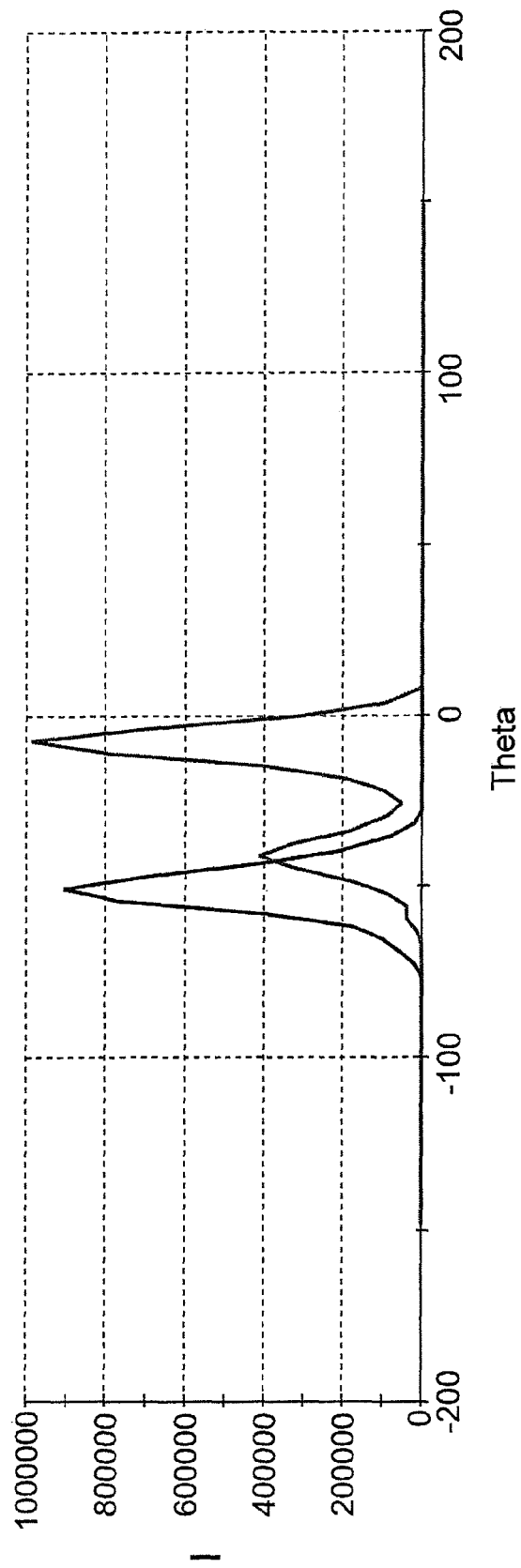
FIG. 8 represents the Z-potential of the conjugate compound obtained in Example 1, recorded by a Malvern Nano Zs Zetasizer, where I represents the intensity and zed represents the potential in mV.

The Z potential of the conjugate compound was determined. The conjugation of the derivatised HA oligomers with a nanoparticle induces a displacement of the Z potential peak to −19.1 mV, as shown in FIG. 8, as compared to the −50.8-mV peak corresponding to the non-conjugated gold nanoparticles.

Example 2

Obtainment of a Conjugate Compound

Example 2.1

Functionalisation of Gold Nanoparticles with HA Oligomers 2.1.1 Enzymatic Hydrolysis of an HA Polymer The HA polymer (HA, sodium salt, of Streptococcus eq., Sigma-Aldrich) was depolymerised by the action of the enzyme ("Bovine Testicular Hyaluronidase (BTH)") hyaluronate 4-glucanohydrolase (E.C. 3.2.1.35) (Hyaluronidase Type I-S, Sigma-Aldrich). 5*104 U of BTH were added to a solution containing 5 mg of HA in 25 ml of aqueous buffer solution (100 mM sodium phosphate, 150 mM sodium chloride, pH 5.3) and stirred for 40 hours at 37° C. The enzymatic reaction was stopped by boiling the sample for 20 minutes. (Glycobiology, July 2002; 12(7):421-6).

2.1.2 Purification of the HA Oligomers

The mixture of HA oligomer fragments was centrifuged at 10,000 rpm for 30 minutes and the supernatant was concentrated and lyophilised. Subsequently, the HA oligomers were purified by means of Centricon Plus 20 centrifugation tubes with a molecular weight cut-off of 10 kDa. Finally, a mixture of HA oligomers with sizes between 2 and 26 monomers was obtained (Glycobiology, July 2002; 12(7):421-6), which was used in the following step.

2.1.3 Derivatisation of the HA Oligomers (21-monomers)

The free carboxyl groups (—COOH) of glucuronic acid present throughout the chain were derivatised with a linker by the formation of an amide bond, using the carbodiimide method. The HA oligomer (8 KDa) (0.1 g, approx. 12.5 mmol) was dissolved in 25 ml of distilled water, stirred for 30 minutes and, subsequently, the pH was adjusted to 5-5.5 with 0.1 N HCl (sometimes, depending on the commercial company wherefrom the HA is acquired, there is no need to adjust the pH, since it is already below 5). An excess of 1-ethyl-3-(3-dimethylaminopropyl)-carbodiimide hydrochloride (EDC) (0.25 g) and N-hydroxysuccinimide (NHS) (0.15 g) was added (the pH was adjusted to 5.5 as necessary) and the reaction was stirred for 30 additional minutes. A quantity of cystamine HCl equal to 0.3 g (the pH changed to 4.3) was added and the reaction was stirred overnight, for approx. 12 hours. Finally, dithiotreitol (DTT) (0.31 g) was added and the reaction stirred for 2 additional hours. The mixture of the resulting reaction was exhaustively dialysed with a dyalisis membrane with a molecular weight cut-off of 3,500 Da against (i) NaCl (30 g, 100 mM)+0.1 N HCl (15 ml, 0.3 mM) (4 days) and (ii) 0.1 N HCl (15 ml, 0.3 mM) (4 days), and, finally, against demineralised distilled water (2 days).

2.1.4 Conjugation of Gold Nanoparticles with Derivatised HA Oligomers (21-monomers)

The 8-nm gold nanoparticles obtained in Example 1.1 were conjugated with the derivatised oligomers (21-monomers)

obtained in 2.1.3, by the addition of 100 μl of a 1.5 mM solution of derivatised oligomers per 5 ml of nanoparticle solution. The reaction was performed at ambient temperature under magnetic stirring for 30 minutes. The reaction was stopped by decreasing the temperature to 4° C. The purification was performed by dialysis (MWCO 16 kDa) against sodium citrate (2.3 mM, 3.25 g/5 l $H_2O$).

Example 3

Obtainment of a Conjugate Compound

Example 3.1

Conjugation of Gold Nanoparticles with a Derivatised HA Polymer

The 8-nm gold nanoparticles were conjugated with a derivatised HA polymer, by the addition of 100 μl of a 1.5 mM solution of thiopropionyl hydrazide-HA (Glycosil™) per 5 ml of gold nanoparticle solution. The reaction was performed at ambient temperature under magnetic stirring for 30 minutes (Macromolecules 2006, 39, 23-25). The reaction was stopped by decreasing the temperature to 4° C.

Example 3.2

Characterisation of the Conjugate Compound 3.2.1 Visualisation by Transmission Electron Microscopy (TEM)

TEM images of both the gold nanoparticles (FIG. 10-A) and the conjugate (FIG. 10-B) were captured in order to show the different morphology adopted by the conjugate of gold nanoparticles with HA polymer. The samples for the TEM studies were prepared by depositing a drop of the corresponding aqueous solution of gold nanoparticles or HA-gold nanoparticle conjugate, on TEM grids coated with carbon.

3.2.2 UV-Vis Spectrum

The UV-Vis absorption spectra of the solutions of gold nanoparticles and the conjugate compound obtained were recorded. The citrate-stabilised gold nanoparticles show a characteristic peak at 521.2 nm. On the other hand, when they are conjugated with HA, a displacement of the absorption peak to a higher wavelength takes place, in this case to 523.8 nm.

3.2.3 Z Potential Spectrum of the Conjugate Compound

Figure 12:
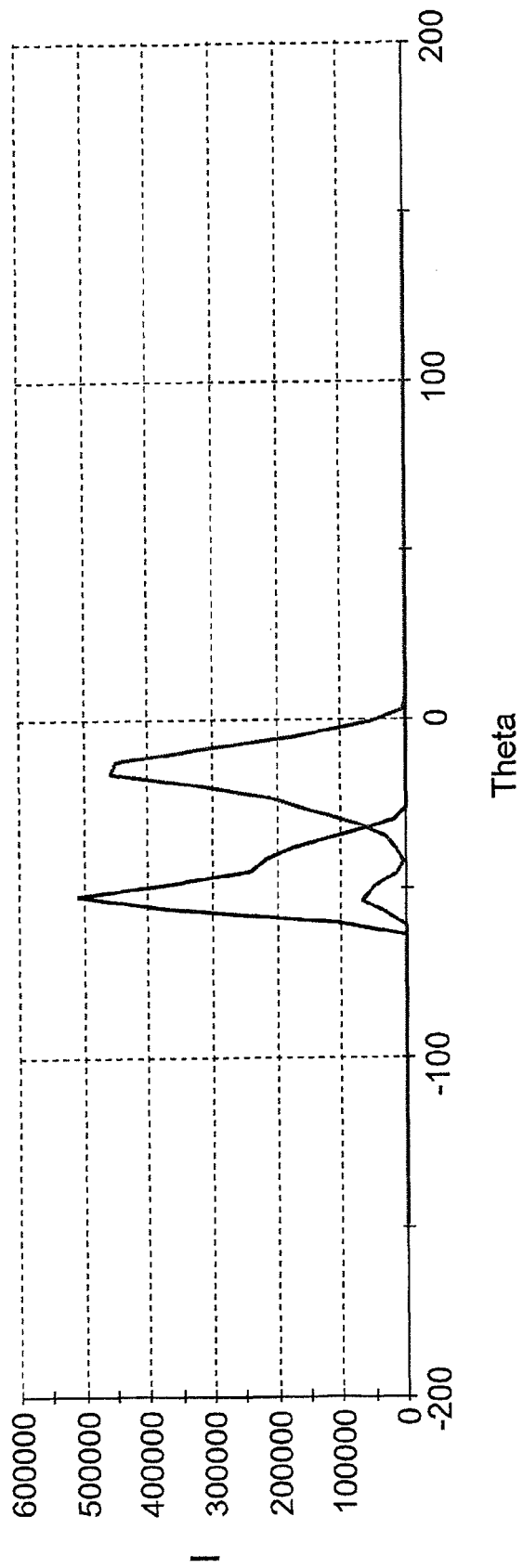
FIG. 12 represents the Z-potential of the conjugate compound obtained in Example 3, recorded by a Malvern Nano ZS Zetasizer, where I represents the intensity and zed represents the potential in mV.

The Z potential was determined. The conjugation of the derivatised HA oligomers with nanoparticles induces a displacement of the Z potential peak to −18.2 mV, as shown in FIG. 12, as compared to the −48.5-mV peak corresponding to the non-conjugated gold nanoparticles.

The invention claimed is:

1. A conjugate compound that comprises one metal nanoparticle and more than one hyaluronic acid (HA) oligomer derivatised through, at least, one chemical bond with at least one linker that comprises an —S— group, whereby each derivatised HA oligomer binds to the metal nanoparticle, provided that when the HA oligomer has a number of monomers n, and n>1,000, and the nanoparticle is a gold nanoparticle with a size of 20 nm, the linker is other than $H_2N$—$CH_2$—$CH_2$—SH.

2. The conjugate compound, as claimed in claim 1, wherein each of the HA oligomers is derivatised with one linker through one chemical bond, and wherein each linker binds each HA oligomer to the metal nanoparticle.

3. The conjugate compound, as claimed in claim 1, wherein each of the HA oligomers is derivatised with at least two linkers, which bind each HA oligomer to the metal nanoparticle.

4. The conjugate compound, as claimed in claim 1, wherein the metal nanoparticle is a nanoparticle comprising a metal or metal oxide selected from the group consisting of Au, Ag, Pt, Co, Fe, an oxide of Au, Ag, Pt, Co, or Fe, and $TiO_2$.

5. The conjugate compound, as claimed in claim 4, wherein the metal nanoparticle is a gold nanoparticle.

6. The conjugate compound, as claimed in claim 4, wherein the metal nanoparticle has an average diameter size between 2 and 100 nm.

7. The conjugate compound, as claimed in claim 1, wherein at least one of the HA oligomers is derivatised through at least one —CONH— amide chemical bond, formed between a carboxylic acid group of an HA oligomer and a linker with the general formula $H_2N$—$R_1$—S—$R_2$, wherein:

$R_2$ represents a first substituent selected from the group consisting of H, —$CH_3$, —$(CH_2)_n$—$CH_3$, —$(CH_2)_n$—CH=$CH_2$ and —S—$R_1$—$NH_2$ and $R_1$ represents a second substituent selected from the group consisting of —$(CH)_n$—, —(CH)(COOH)$(CH_2)_n$—, and —NH—CO—$(CH_2)_n$—, where n represents an integral number between 1 and 20.

8. The conjugate compound as claimed in claim 1, wherein at least one of the HA oligomers is derivatised in accordance with one of the following alternatives:

a) through, at least, one —COO— ester chemical bond, formed between a carboxylic acid group of an HA oligomer and a linker with the general formula HO—$R_1$—S—$R_2$, or b) through, at least, one ether chemical bond, —O—, formed between an —OH group of the HA oligomer and a linker with the general formula LG-$R_1$—S—$R_2$, where $R_2$ represents a first substituent selected from the group consisting of H, —$CH_3$, —$(CH_2)_n$—$CH_3$, —$(CH_2)_n$—CH=$CH_2$ and —S—$R_1$—$NH_2$, and $R_1$ represents a second substituent selected from the group consisting of —$(CH)_n$— and —(CH)(COOH)$(CH_2)_n$—, where n represents an integral number between 1 and 20; and LG represents a leaving group.

9. A method of preparing a conjugate compound as claimed in claim 8, selected from the group consisting of the following processes:

Process A that comprises the steps of:

(i) enzymatic hydrolysis of an HA polymer;

(ii) obtaining the HA oligomer fragments;

(iii) derivatizing the HA oligomer fragments by chemical reaction with one linker that comprises an —S— group, through at least one amide, ester or ether chemical bond; and (iv) conjugating derivatised HA oligomer fragments obtained in step (iii) with one metal nanoparticle;

Process B that comprises the steps of:
  (i) derivatizing an HA polymer by chemical reaction with one linker that comprises an —S— group, by forming at least one amide, ester or ether chemical bond;
  (ii) enzymatic hydrolysis of the derivatised HA polymer;
  (iii) obtaining derivatised HA oligomer fragments; and
  (iv) conjugating the fragments obtained in the step (iii) with one metal nanoparticle;

Process D that comprises the steps of:
  (i) enzymatic hydrolysis of a derivatised HA polymer with one linker that comprises an —S— group, through at least one amide, ester or ether chemical bond;
  (ii) obtaining derivatised HA oligomer fragments; and
  (iii) conjugating derivatised HA oligomer fragments obtained in step (ii) with one metal nanoparticle;

Process F that comprises the steps of:
  (i) biosynthesis of an HA oligomer fragment by the action of a Hyaluronate Synthase;
  (ii) derivatisation of the biosynthesised oligomer fragment with one linker that comprises an —S— group, through at least one amide, ester or ether chemical bond;
  (iii) obtaining derivatised HA oligomer fragments; and
  (iv) conjugating derivatised HA oligomer fragments obtained in step (iii) with one metal nanoparticle; and Process G that comprises the steps of:
  (i) starting from an HA polymer or oligomer,
  (ii) derivatising it with at least one linker that comprises an —S— group, through at least one amide, ester or ether chemical bond;
  (iii) conjugating a derivatised HA polymer or oligomer with one metal nanoparticle, and
  (iv) obtaining the conjugate compound.

10. The conjugate compound, as claimed in claim 8, that additionally comprises, at least, another molecule conjugated with the metal nanoparticle.

11. The conjugate compound, as claimed in claim 10, wherein the molecule is a compound selected from the group consisting of peptides, proteins, and HA hydrolysis inhibitors.

12. A cosmetic composition that comprises
  (1) at least one compound selected from the group consisting of:
    (i) a conjugate compound that comprises one metal nanoparticle and more than one hyaluronic acid (HA) oligomer derivatised through, at least, one chemical bond with at least one linker that comprises an —S— group, whereby the derivatised HA oligomer binds to the metal nanoparticle, and
    (ii) a multi-conjugate compound comprising one metal nanoparticle; and more than one HA oligomer derivatised through, at least, one chemical bond with at least one linker that comprises an —S— group, whereby the derivatised HA oligomer binds to the metal nanoparticle, wherein the HA oligomer is derivatised in accordance with one of the following alternatives:
      a) through, at least, one —COO— ester chemical bond, formed between a carboxylic acid group of an HA oligomer and a linker with the general formula HO—$R_1$—S—$R_2$, or
      b) through, at least, one ether chemical bond, —O—, formed between an —OH group of the HA oligomer and a linker with the general formula LG-$R_1$—S—$R_2$, where $R_2$ represents a first substituent selected from the group consisting of H, —$CH_3$, —$(CH_2)_n$—$CH_3$, —$(CH_2)_n$—CH=$CH_2$ and —S—$R_1$—$NH_2$, and
      $R_1$ represents a second substituent selected from the group consisting of —$(CH)_n$— and —(CH)(COOH)$(CH_2)_n$—, where n represents an integral number between 1 and 20; and LG represents a leaving group; and another molecule conjugated with the one metal nanoparticle; and
  (2) at least one physiologically acceptable excipient.

13. The conjugate compound according to claim 7, wherein $R_1$ represents (CH) (COOH) $(CH_2)_n$ where n is 1 or 2.

14. The conjugate compound according to claim 7, wherein $R_2$ represents H, —$CH_3$, —$CH_2$—$CH_3$ or —$CH_2$—CH=$CH_2$.

15. A method for cosmetic treatment comprising applying topically to the skin of a user at least one compound selected from the group consisting of:
  (1) a conjugate compound that comprises one metal nanoparticle and more than one hyaluronic acid (HA) oligomer derivatised through, at least, one chemical bond with at least one linker that comprises an —S— group, whereby one derivatised HA oligomer binds to the metal nanoparticle, and
  (2) a multi-conjugate compound comprising one metal nanoparticle and more than one HA oligomer derivatised through, at least, one chemical bond with at least one linker that comprises an —S— group, whereby the derivatised HA oligomer binds to the metal nanoparticle, wherein the HA oligomer is derivatised in accordance with one of the following alternatives:
    a) through, at least, one —COO— ester chemical bond, formed between a carboxylic acid group of an HA oligomer and a linker with the general formula HO—$R_1$—S—$R_2$, or
    b) through, at least, one ether chemical bond, —O—, formed between an —OH group of the HA oligomer and a linker with the general formula LG-$R_1$—S—$R_2$, where $R_2$ represents a first substituent selected from the group consisting of H, —$CH_3$, —$(CH_2)_n$—$CH_3$, —$(CH_2)_n$—CH=$CH_2$ and —S—$R_1$—$NH_2$, and
    $R_1$ represents a second substituent selected from the group consisting of —$(CH)_n$— and —(CH)(COOH)$(CH_2)_n$—, where n represents an integral number between 1 and 20; and LG represents a leaving group; and another molecule conjugated with the metal nanoparticle.

16. A method for cosmetic treatment comprising injecting into the skin of a user at least one compound selected from the group consisting of:
  (1) a conjugate compound that comprises one metal nanoparticle; and more than one hyaluronic acid (HA) oligomer derivatised through, at least, one chemical bond with at least one linker that comprises an —S— group, whereby one derivatised HA oligomer binds to the metal nanoparticle, and
  (2) a multi-conjugate compound comprising one metal nanoparticle and more than one HA oligomer derivatised through, at least, one chemical bond with at least one linker that comprises an —S— group, whereby the derivatised HA oligomer binds to the metal nanoparticle, wherein the HA oligomer is derivatised in accordance with one of the following alternatives:

a) through, at least, one —COO— ester chemical bond, formed between a carboxylic acid group of an HA oligomer and a linker with the general formula HO—$R_1$—S—$R_2$, or
b) through, at least, one ether chemical bond, —O—, formed between an —OH group of the HA oligomer and a linker with the general formula LG-$R_1$—S—$R_2$,
   where $R_2$ represents a first substituent selected from the group consisting of H, —$CH_3$, —$(CH_2)_n$—$CH_3$, —$(CH_2)_n$—CH=$CH_2$ and —S—$R_1$—$NH_2$, and
   $R_1$ represents a second substituent selected from the group consisting of $(CH)_n$— and —(CH)(COOH)$(CH_2)_n$—, where n represents an integral number between 1 and 20; and LG represents a leaving group; and another molecule conjugated with the metal nanoparticle.

17. The method according to claim 15, wherein the compound topically applied to the skin comprises HA oligomers with a molecular weight below 1,000 kDa.

18. The method according to claim 16, wherein the compound injected into the skin of the user has a molecular weight greater than 500 kDa.

19. A method of preparing a conjugate compound as claimed in claim 7, selected from the group consisting of the following processes:

Process A that comprises the steps of:
   (i) enzymatic hydrolysis of an HA polymer;
   (ii) obtaining the HA oligomer fragments;
   (iii) derivatizing the HA oligomer fragments by chemical reaction with one linker that comprises an —S— group, through at least one amide, ester or ether chemical bond; and
   (v) conjugating derivatised HA oligomer fragments obtained in step (iii) with one metal nanoparticle;

Process B that comprises the steps of:
   (i) derivatizing an HA polymer by chemical reaction with one linker that comprises an —S— group, by forming at least one amide, ester or ether chemical bond;
   (ii) enzymatic hydrolysis of the derivatised HA polymer;
   (iii) obtaining derivatised HA oligomer fragments; and
   (v) conjugating the fragments obtained in the step (iii) with one metal nanoparticle;

Process D that comprises the steps of:
   (i) enzymatic hydrolysis of a derivatised HA polymer with one linker that comprises an —S— group, through at least one amide, ester or ether chemical bond;
   (ii) obtaining derivatised HA oligomer fragments; and
   (iii) conjugating derivatised HA oligomer fragments obtained in step (ii) with one metal nanoparticle;

Process F that comprises the steps of:
   (i) biosynthesis of an HA oligomer fragment by the action of a hyaluronate synthase;
   (ii) derivatisation of the biosynthesised oligomer fragment with one linker that comprises an —S— group, through at least one amide, ester or ether chemical bond;
   (iii) obtaining derivatised HA oligomer fragments; and
   (iv) conjugating derivatised HA oligomer fragment obtained in step (iii) with one metal nanoparticle; and Process G that comprises the steps of:
   (i) starting from an HA polymer or oligomer,
   (ii) derivatising it with at least one linker that comprises an —S— group, through at least one amide, ester or ether chemical bond;
   (iii) conjugating a derivatised HA polymer or oligomer with one metal nanoparticle, and
   (iv) obtaining the conjugate compound.

* * * * *